United States Patent [19]
Kuhn et al.

[11] Patent Number: 5,777,091
[45] Date of Patent: Jul. 7, 1998

[54] PHOSPHONOMETHYLATED CHITOSANS

[75] Inventors: Martin Kuhn, Dornach, Switzerland; Thomas Maier, Schliengen, Germany; Albert Stehlin, Rosenau, France

[73] Assignee: Ciba Specialty Chemicals Corporation, Tarrytown, N.Y.

[21] Appl. No.: 560,264

[22] Filed: Nov. 21, 1995

[30] Foreign Application Priority Data

Nov. 24, 1994 [CH] Switzerland ............... 03 544/94

[51] Int. Cl.$^6$ ............... C08B 37/08; C11D 3/395
[52] U.S. Cl. ............... 536/20; 536/124; 252/186.1; 252/188.1
[58] Field of Search ............... 536/20, 124; 252/186.1, 252/188.1

[56] References Cited

U.S. PATENT DOCUMENTS

| | | | |
|---|---|---|---|
| 3,288,846 | 11/1966 | Irani et al. | 562/16 |
| 3,879,376 | 4/1975 | Vanlerberghe | 536/20 |
| 5,646,271 | 7/1997 | Stehlin et al. | 536/123.1 |

FOREIGN PATENT DOCUMENTS

| | | |
|---|---|---|
| 0392396 | 10/1990 | European Pat. Off. |
| 628655 | 12/1994 | European Pat. Off. |
| 2222733 | 11/1972 | Germany. |
| 4227019 | 2/1994 | Germany. |

OTHER PUBLICATIONS

Redmore, J. Org. Chem. vol. 43, No. 5 (1978), 992–7.

Primary Examiner—Kathleen K. Fonda
Attorney, Agent, or Firm—Kevin T. Mansfield

[57] ABSTRACT

Phosophonomethylated chitosans containing repeating units of formula

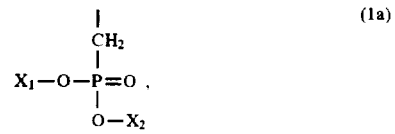

wherein $R_1$ is hydrogen or a radical of formula $$\begin{array}{c} CH_2 \\ | \\ X_1-O-P=O \\ | \\ O-X_2 \end{array} \quad (1a)$$

$R_2$ is a radical of formula (1a), $X_1$ and $X_2$ are each independently of the other hydrogen, $C_1-C_5$alkyl or an alkali metal ion or ammonium ion and n is 50 to 4000, have versatile utilities as sequestrants, stabilizers for bleaching agents as well as humectants in cosmetic compositions.

4 Claims, No Drawings

PHOSPHONOMETHYLATED CHITOSANS

The present invention relates to phosphonomethylated chitosans, to the preparation of these compounds, to the use thereof as sequestrants, complexing agents or stabilisers for bleaching agents, to a bleaching liquor containing said novel phosphonomethylated chitosans, to a process for bleaching cellulosic fibre materials, to the fibre material treated by said bleaching process, to a process for preventing the adherence to and/or formation of solid deposits on inorganic or organic substrates, and to the use of the novel chitosans as humectants for the skin and mucous membranes.

Phosphonomethylation is known, inter alia from *J. Org. Chem.* 31, 1503–1607 (1966). It proceeds in analogy to the Mannich reaction by reacting amines that carry at least one —NH group, in the acid pH range, with phosphorous acid and formaldehyde. In this reaction the group of formula

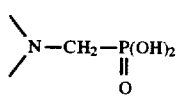

is formed from the

group of the amine.

Products containing such groups are used as sequestrants for polyvalent metal ions.

The present invention has for its object the provision of novel phosphonomethylated compounds which can be prepared from readily accessible materials that occur in nature.

This object is achieved with phosphonomethylated chitosans which contain repeating units of formula

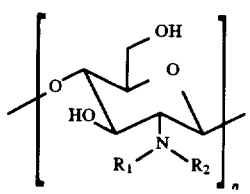 (1)

wherein $R_1$ is hydrogen or a radical of formula

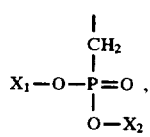 (1a)

$R_2$ is a radical of formula (1a), $X_1$ and $X_2$ are each independently of the other hydrogen, $C_1$–$C_5$alkyl or an alkali metal ion or ammonium ion and n is 50 to 4000.

$C_1$–$C_5$Alkyl is straight-chain or branched alkyl, typically methyl, ethyl, n-propyl, isopropyl, n-butyl, sec-butyl, tert-butyl, amyl, isoamyl or tert-amyl.

Suitable alkali metals are potassium or, preferably, sodium.

Suitable compounds are those containing repeating units of formula

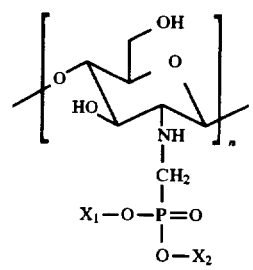 (2)

wherein $X_1$, $X_2$ and n are as defined for formula (1).

Preferred compounds are suitably compounds of formula (1) or (2), wherein $X_1$ and $X_2$ are each independently of the other alkali metal, and n is 200 to 2000.

The phosphonomethylation of chitosan is carried out in per se known manner by reacting a compound containing repeating units of formula

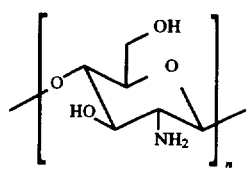 (1a)

with formaldehyde and phosphorous acid in acidic medium, preferably a medium containing hydrochloric acid. The pH of the reaction mixture is 0 to 4, preferably 0 to 2. The reaction can be carried out with particular advantage in the temperature range from 80° to 120° C. The reaction times are from 5 to 24 hours, preferably from 10 to 20 hours.

Upon completion of the reaction, the pH of the resultant solution is adjusted to 6–9, preferably to 7–8, with a strong base, preferably dilute aqueous sodium hydroxide. The purification of the product solution is conveniently effected by reverse osmosis and subsequent lyophilisation of the concentrate so obtained.

The invention further relates to the preparation of the novel phosphonomethylated chitosans.

The novel chitosan derivatives are polyampholytes with film-forming and chelating properties, even in the presence of alkaline earth metal ions. Owing to their pronounced complexing action for heavy metal ions even in low concentration, the products can be used for removing such cations from contaminated water, conveniently for removing iron or copper ions from mains water. In addition, they can be used as sequestrants in the food industry, the pharmaceutical industry and the textile industry, as well as detergents, singly or in conjunction with cationic, anionic or neutral detergents.

The novel chitosan derivatives have a surprisingly good capacity for complexing metal ions, whereby the precipitation of polymeric metal salts, especially in the case of polyvalent cations, can be favourable influenced or prevented. Furthermore, they have a modulating action in crystallisation processes, especially on the formation of seed crystals, their growth and the morphology of the resultant crystals and their size distributions, as well as on the aggregation and adhesion properties. They are therefore suitable for water treatment to prevent the formation of deposits in water-conducting systems (water treatment plants), for example on the walls of containers, membranes or conduits. They can also be used for the treatment of textiles, conveniently cotton. The novel phosphonomethylated chitosans also prevent the formation of deposits of inorganic and/or organic components. They are therefore also suitable for use as additives for dental care products for the prevention of dental plaque, as well as additives for detergent formulations.

The novel phosphonomethylated chitosans further find utility as bleaching stabilisers in e.g. detergent compositions or in the bleaching of textiles, cellulose or paper stock. In this utility, the chelating agents bind the calcium, magneisum, iron, copper or manganese ions present in the bleaching liquors and simultaneously prevent the precipitation of akaline earth metal carbonate or hydroxide and the decomposition of the per compound.

A further object of the invention is thus the application process for bleaching fibre cellulosic materials. The process comprises treating the fibre material with an aqueous liquor which contains at least the novel phosphonomethylated chitosan, an alkali metal hydroxide, a water-soluble magnesium salt and a per compound.

The aqueous bleaching liquors for carrying out the application process, which comprises the use of the novel phosphonomethylated chitosans, likewise constitute an object of the invention.

The per compound may suitably be selected from the group consisting of alkali metal peroxodisulfates and, preferably, alkali metal peroxosulfates, preferred compounds being potassium and, more particularly, sodium peroxodisulfate or peroxosulfate. Sodium peroxodisulfate ($Na_2S_2O_8$), which is normally used as a solid, is very particularly preferred. The preferred per compound is hydrogen peroxide which, owing to its superior stability, is normally used as a concentrated solution of c. 30–60% by weight.

Particularly suitable alkali metal hydroxides are potassium or, preferably, sodium hydroxide, preferably in the form of a concentrated solution of c. 30% by weight, or as solid potassium or, preferably, sodium hydroxide.

In addition to comprising the novel formulation, alkali metal hydroxide and a per compound, the bleaching liquors may also comprise an optional component selected from the group consisting of wetting agents or surfactants, antifoams or deaerators and/or fluorescent whitening agents.

A wetting agent or surfactant will usually be added to the bleaching liquors as optional component if the cellulose component of the cellulosic fibre material to be treated is in the untreated state or, preferably, consists of raw cotton. The wetting agent or surfactant is suitably an anionic or nonionic surfactant, but preferably a mixture thereof. Preferred anionic surfactants are typically alkyl aryl monosufonates, fatty acid condensates, proteolysis products or salts thereof and, most preferably, alkyl monosulfonates and alkylbenzenemonosulfonic acids containing 12 to 22 carbon atoms in the alkyl moiety. Preferred nonionic surfactants are typically polyadducts of alkylene oxides, preferably propylene oxide and, more particularly, ethylene oxide, with alkylphenols containing 4 to 12 carbon atoms in the alkyl moiety, preferably fatty acid amides and, more particularly, fatty alcohols or end-capped fatty alcohols. Polyadducts of ethylene oxide with fatty alcohols are especially preferred and are very particularly preferred in admixture with the alkyl monosulfonates of the indicated type. Further suitable components of these mixtures are also silicone surfactants.

The addition of an antifoam or deaerator as optional component of the bleaching liquor is indicated especially if said liquor contains a wetting agent or surfactant. The antifoam or deaerator is typically a higher alcohol, preferably isooctanol, but is preferably a silicone-based compound, most preferably a silicone oil emulsion.

The fluorescent whitening agents which may also be added to the bleaching liquor as optional component to impart particularly high whiteness to the treated materials will usually belong to the styryl and stilbene series, typically including distyrylarylenes, diaminostilbenes, ditriazolylstilbenes, phenylbenzoxazolylstilbenes, stilbenenaphthotriazoles and dibenzoxazolylstilbenes. Preferred fluorescent whitening agents are those of the distyrylbiphenyl or bis(triazinyl)aminostilbene type which contain sulfonic acid groups, e.g. sulfonated bis(styryl)biphenyl) and bis(triazinyl) derivatives, preferably the bis(phenylaminomorpholino-s-triazinyl)stilbenedisulfonic acids obtained in the form of alkali metal salts, preferably as potassium or, preferably, sodium salts. These fluorescent whiteners will preferably be used as commercially obtainable aqueous formulations of c. 20–30% by weight.

The application process for bleaching cellulosic fibre materials using the novel bleach comoposition is carried out by per se knowh methods. A distinction is made here between a treatment in long liquors, a cold pad-batch method and an immersion bleaching process.

In long liquors the material is subjected to a treatment at a liquor to goods ratio of about 1:3, e.g. in a jigger, to about 1:40, e.g. on a winchbeck, for about 1 to 3 hours at elevated temperature. The treatment temperature is in the range from about 40° to 140° C., preferably from 60° to 100° C., under normal conditions, i.e. under atmospheric pressure or above 100° C., preferably in the range from 105° to 140° C., under so-called HT conditions (HT=high-temperature).

The immersion bleaching treatment is carried out under the same application conditions, except that the concentration of per compound and alkali is higher.

In the cold pad-batch bleaching process, the material to be treated is impregnated by immersion in a padding liquor and then pinched-off, the padding liquor usually having a temperature of 20° to 95° C. Impregnation is preferably carried out at room temperature. The chemicals applied by impregnation then act on the textile material, the treatment time, the temperature and the concentration of the chemicals being in direct relation to one another, and the chosen conditions depending on the nature of fibre material and, in particular on the apparatus used. Thereafter the impregnated and preferably rolled-up goods are stored at room temperature (15°–30° C.) for 3 to 24 hours, the batching time depending on the type of bleaching bath. The fibre materials are subsequently thoroughly rinsed first with hot water of 90°–98° C., then with warm and, finally, with cold water, if required neutralised with e.g. acetic acid and then hydroextracted and dried preferably at elevated temperature of up to e.g. 150° C.

Depending on whether they are long liquors, immersion liquors or cold pad-batch bleaching liquors, the aqueous bleaching liquors are formulated as indicated.

The long-bleaching liquors comprise 0.5 to 5 g/kg, preferably 0.5 to 2 g/kg, of the nove aqueous phosphonomethylated chitosan, 0.1 to 1%, preferably 0.2 to 0.5%, of a water-solubl magnesium salt, 1 to 6 ml/kg, preferably 2 to 5 ml/kg, of a per compound 1 to 5 g/kg, preferably 0.1 to 2 g/kg, of an alkali meta hydroxide, 0.2 to 2 g/kg, preferably 0.5 to 1 g/kg, of a wetting ager or surfactant, 0 to 0.5 g/kg or 0.05 to 0.5 g/kg of an antifoam c deaerator, and 0 to 5 g/kg, preferably 1.5 to 4 g/kg, of a fluorescer whitening agent.

The immersion bleaching liquors comprise 0.5 to 5 g/kg, preferably 0.5 to 2 g/kg, of the novel aqueous phosphonomethylated chitosan, 0.5 to 1.5%, preferably 0.2 to 1%, of a water-soluble magnesium salt, 2 to 12 ml/kg, preferably 4 to 10 ml/kg, of a per compound, 1 to 5 g/kg, 1.5 to 4 g/kg, of an alkali metal hydroxide, 0 to 2 g/kg, preferably 0.5 to 1 g/kg, of a wetting agent or surfactant, 0 to 0.5 g/kg, preferably 0.05 to 0.5 g/kg, of an antifoam or deaerator, and 0 to 30 g/kg, preferably 2 to 10 g/kg, of a fluorescent whitening agent.

The cold pad-batch bleaching liquors comprise 5 to 15 g/kg, preferably 8 to 12 g/kg, of the novel aqueous phosphonomethylated chitosan, 0.5 to 2.5%, preferably 1 to 1.5%, of a water-soluble magnesium compound, 30 to 60 ml/kg, preferably 50 to 60 ml/kg, of a per compound, 20 to 50 g/kg, preferably 25 to 40 g/kg, of an alkali metal hydroxide, 1 to 6 g/kg, preferably 3 to 6 g/kg, of a wetting agent or surfactant, 0 to 2 g/kg, preferably 0.05 to 1 g/kg, of an antifoam or deaerator, and 0 to 6 g/kg, preferably 2 to 6 g/kg, of a fluorescent whitening agent.

The cellulosic fibre material to be treated may be in any form of presentation, typically as loose material, yarn, woven or knitted goods. It will normally always consist of textile fabrics that are made from pure textile cellulose fibres or from blends of textile cellulose fibres with synthetic textile fibres.

Cellulosic fibres are typically those from regenerated cellulose such as viscose rayon or viscose, those from natural cellulose such as hemp, linen, jute and ramie and, in particular, cotton. Synthetic fibres are suitably those made from polyacrylonitrile and, in particular, from polyester and polyamide.

Cotton or regenerated cellulose fabrics or blends of cotton and polyester and of cotton and polyamide are particularly suitable for treatment in the practice of this invention. Cotton woven and knitted goods are preferred. Materials that have been prewashed with surfactants are also suitable. It is also possible to bleach sized cotton fabrics, in which case bleaching is carried out before or, preferably, after sizing.

The fibre materials treated with the novel bleach formulation are distinguished by their freedom from husks, their low ash content and, in particular, by their superior whiteness. The cellulose or cellulose component of the bleached material exhibits no damage or no substantial reduction in the degree of cellulose polymerisation (=DP=average degree of polymerisation). The formulation of this invention effects a particularly high stabilisation, especially in bleaching liquors that have a pH>11. Traces of heavy metals, especially iron(III) ions, which can cause spontaneous decomposition of the per compounds present in the bleaching liquor, are effectively neutralised. One consequence thereof is that the original content of active oxygen of the bleaching liquors is retained over a considerable period of time (e.g. up to 5 days) or decreases only insignificantly, by at most 10%. An excellent bleaching effect is nevertheless achieved. The liquors are thus stable in regard to their content of active oxygen and can be used for some time. Moreover, the novel formulation inhibits crystallinity with respect to water hardness. A fabric treated with the novel formulation has excellent rewettability. A significant advantage of the novel formulation is its good biodegradibility.

A further object of the invention is the use of the novel phosphonomethylated chitosans for preventing the adhesion to and or formation of solid deposits on inorganic or organic substrates. The deposits, which often have a crusty consistency, may be composed of inorganic and/or organic components, typically salts and polymers, also of biological origin. The substrates may be inorganic and/or organic materials or biological materials, for example glass, ceramics, meals and alloys, natural or synthetic plastic materials, paper, textiles, leather or vegetable or animal organs or tissues.

Hence a further object of the invention is a process for preventing the adhesion to and or formation of solid deposits on inorganic or organic substrates, which process comprises adding to a fluid or a composition that is in contact with an inorganic or organic substrate the novel phosphonomethylated chitosan, preferably in an amount of 0.01 to 20% by weight, most preferably 0.1 to 10% by weight.

The novel phosphonomethylated chitosans have film-forming properties. The evaporation of aqueous solutions leads to the formation of transparent, solid and water-containing films which are permeable to air and moisture. By virtue of this property and their hydropectic action, they are also suitable for use as humectants for the skin or mucous membranes in cosmetic and pharmaceutical compositions, typically skin and hair care products and deodorants. The novel phosphonomethylated chitosans are able to bind iron ions on the skin and can therefore replace the EDTA customarily used in creams, especially sun creams.

Hence another object of the invention is a cosmetic composition comprising at least one compound containing repeating units of formula (1) as well as cosmetically acceptable carriers or adjuvants.

The novel cosmetic composition comprises for example 0.001 to 15% by weight, such as 0.1 to 15% by weight, preferably 0.001 to 10% by weight, and most preferred 0.002 to 5% by weight, based on the total weight of the composition, of a compound that contains repeating units of formula (1) as well as cosmetically acceptable carrier or adjuvants.

The cosmetic composition can be prepared by physically mixing a compound that contains repeating units of formula (1) with the adjuvants by conventional methods, typically by simple stirring of the two components.

The novel cosmetic composition can be formulated as water-in-oil or oil-in-water emulsion, as oil-in-oil alcoholic solution, as vesicular dispersion of an ionic or nonionic amphiphilic lipid, as gel, solid stick or as aerosol formulation.

Any conventional emulsifier can be used for the novel cosmetic formulations, conveniently one or more than one ethoxylated ester of natural derivatives, for example polyethoxylated esters of hydrogenated castor oil; or a silicone oil emulsifier such as silicone polyol; a fatty acid or ethoxylated fatty acid soap; an ethoxylated fatty alcohol; a sorbitan ester or ethoxylated sorbitan ester; an ethoxylated fatty acid; or an ethoxylated glyceride.

The cosmetic formulation may also comprise further components such as emollients, emulsion stabilisers, suntan promoters, thickeners, moisture retainers such as glycerol, preservatives, perfumes and colorants.

The novel phosphonomethylated chitosans also have a viscosity increasing and dispersing action in aqueous solutions. They are thus suitable for use as additives in suspensions, emulsions and aqueous solutions, for example in the manufacture of foodstuffs or active substance concentrates as well as in dye and pigment formulations.

The novel phosphonomethylated chitosans can also have biocidal activity, typically bacteriostatic, fngistatic or algidicic activity.

In the following Examples parts and percentages are by weight.

PREPARATION OF THE NOVEL PHOSPHONOMETHYLATED CHITOSANS

Example 1

A 60 l enamel kettle is charged at room temperature with 2.163 parts of chitosan (flakes), 2.23 parts of phosphorous acid, 6.9 parts of water, and 7.0 parts of hydrochloric acid (32%).

The resultant beige flocculent suspension is quite readily stirrable. The batch is heated to 80° C. and, at this temperature, 4.27 parts of formaldehyde (37%) are added dropwise over 20 minutes. The mixture now becomes distinctly more fluid and browner in colour.

The mixture is allowed to react for 18 hours at the set temperature. After 2 hours the batch is dark brown and is then cooled to room temperature and adjusted to pH 7.5 with about 9 parts of 50% aqueous sodium hydroxide solution.

The brown product solution is filled into a container and subjected to reverse osmosis. The residual concentrate is lyophilised, affording the product containing repeating units of formula

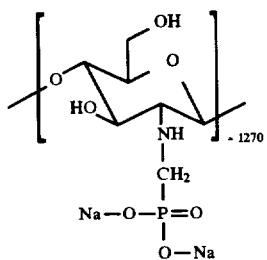

(101)

Example 2

Determination of the complexing capacity and dispersing power a. Determination of the Ca complexing capacity 1 g of the compound of formula (101) is dissolved in c. 80 ml of deionised water and the solution is adjusted to pH 8 with iN NaOH. Then 2 ml of 10% sodium carbonate solution are added as precipitant, the pH is adjusted to 12 with NaOH, and the batch is bulked to 100 ml. A nephelometer optrode is immersed in the solution and calibrated at stage 2 (measuring range 10–20'000 NTU; NTU= "nephelometric turbidity units") to 0. Titration is carried out, with stirring, with 0.5M calcium acetate in increments of 0.1 ml at one minute intervals until the onset of turbidity. The changes in the pH during titration are corrected correspondingly.

The Ca complexing capacity is calculated in accordance with the following formula:

$$\text{mg complexed Ca/g product} = \frac{\text{ml 0.5 M calcium acetate} \times 20}{\text{weight of product}}$$

The value of 168 mg/g calculated for the compound of formula (101) shows that the novel phosphonomethylated chitosan is a compound with good complexing capacity.

b. Determination of the $CaCO_3$ dispersing power

The procedure described in a. is repeated, except that 10 ml of 10% sodium carbonate solution is used instead of 2 ml of 10% sodium carbonate solution.

The $CaCO_3$ dispersing power is calculated in accordance with the formula shown in a.

The value of 50 mg/g calculated for the compound of formula (101) shows that the novel phosphonomethylated chitosan is a compound with good $CaCO_3$ dispersing power.

Example 3

Use in a cosmetic composition

Preparation of a sun protection cream:

| | |
|---|---|
| 7.5 parts | of octylmethoxy cinnamate |
| 5 parts | of octyl salicylate, |
| 5 parts | of methyl anthranilate |
| 2 parts | of isocetyl alcohol |
| 2 parts | of cetearyl alcohol |
| 1.5 parts | of glyceryl stearate |
| 1.0 part | of PEG-40 stearate |
| 1.0 part | of Methicon |
| 0.75 part | of cetyl alcohol |
| 0.25 part | of tocopheryl acetate, and |
| 6 parts | of zinc oxide | are mixed and the mixture is heated to 75°–80° C. Afterwards 0.5 part of magnesium aluminium silicate is then dispersed with a commercially available ball, vibration or hammer mill in 63.8 parts of water.

To this dispersion is then added 0.5 part of xanthane gum and the batch is mixed until a homogeneous solution forms. Then 0.2 part of the compound of formula (101) is added and the solution is heated to 75°–80° C. To this solution are then added, with stirring, the compounds initially mixed and heated to 75°–80° C. After grinding for 10–15 minutes and cooling to 40° C., 1 part of propylene glycol is added. Stirring is continued and the batch is cooled to room temperature.

The composition is suitable for use as a moisturising sun protection cream.

What is claimed is:

1. A phosphonomethylated chitosan containing repeating units of formula

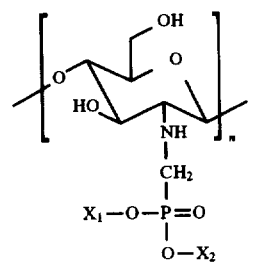

(2 wherein $X_1$ and $X_2$ are each independently of the other hydrogen $C_1$–$C_5$alkyl or an alkali metal ion or ammonium io and n is 50 to 4000.

2. A chitosan according to claim 1, wherein in formula (2) $X_1$ and $X_2$ are each independently of the other alkali metal and
n is 200 to 2000.

3. A process for the preparation of a chitosan as claimed in claim 1, which comprises reacting a compound containing repeating units of formula

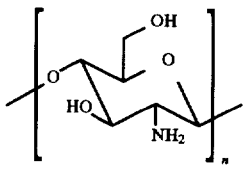
(1a)

with formaldehyde and phosphorous acid in acidic medium, at pH 0 to 4, in the temperature range from 80° to 120° C. and in a reaction time from 5 to 24 hours, to give the compound containing repeating units of formula (2), wherein n is as defined for formula (2).

4. A bleaching liquor comprising at least one per compound, an alkali metal hydroxide, a water-soluble magnesium salt and a chitosan as claimed in claim 1.

* * * * *